United States Patent [19]

Bare et al.

[11] 4,365,634
[45] Dec. 28, 1982

[54] MEDICAL ELECTRODE CONSTRUCTION

[75] Inventors: Rex O. Bare; Earl F. Robinson, both of Lawerance, Kans.

[73] Assignee: C. R. Bard, Inc., Murray Hill, N.J.

[21] Appl. No.: 100,904

[22] Filed: Dec. 6, 1979

[51] Int. Cl.³ .............................................. A61B 5/04
[52] U.S. Cl. .................................. 128/640; 128/798; 128/803
[58] Field of Search ............................. 128/639–641, 128/644, 783, 798, 802, 803

[56] References Cited

U.S. PATENT DOCUMENTS

| | | | |
|---|---|---|---|
| 3,805,769 | 4/1974 | Sessions | 128/641 |
| 3,911,906 | 10/1975 | Reinhold, Jr. | 128/641 |
| 3,989,035 | 11/1976 | Zuehlsdorff | 128/641 |
| 3,993,049 | 11/1976 | Kater | 128/641 |
| 3,998,215 | 12/1976 | Anderson et al. | 128/641 |
| 4,008,721 | 2/1977 | Burton | 128/708 |
| 4,050,453 | 9/1977 | Castillo et al. | 128/640 |
| 4,051,842 | 10/1977 | Hazel et al. | 126/640 |
| 4,066,078 | 1/1978 | Berg | 128/641 |
| 4,082,086 | 4/1978 | Page et al. | 128/640 |
| 4,082,087 | 4/1978 | Howson | 128/640 |
| 4,257,424 | 3/1981 | Cartmell | 128/641 |

FOREIGN PATENT DOCUMENTS 1441622 7/1976 United Kingdom ............. 128/630

Primary Examiner—Lee S. Cohen
Attorney, Agent, or Firm—Trexler, Bushnell & Wolters, Ltd.

[57] ABSTRACT

There is disclosed an electrode construction of the type including a terminal arrangement and support structure for said terminal arrangement, said support structure adapted for the transcutaneous application of the electrode to a patient. The support structure may be fabricated from a layer of foam or microporous material, or plural layer employing a combination of both, or from a layer of conductive adhesive. The terminal arrangement may be of single terminal or multi-terminal design, and is provided by a conductive pattern printed on a semi-flexible plastic-like sheet, wherein said pattern is printed with a conductive ink of the type employing a conductive metal, such as silver, in a binder composition. The disclosure also contemplates novel structure for connection of the electrode to a lead wire, as well as several novel, overall designs for the construction of the electrode support means.

9 Claims, 29 Drawing Figures

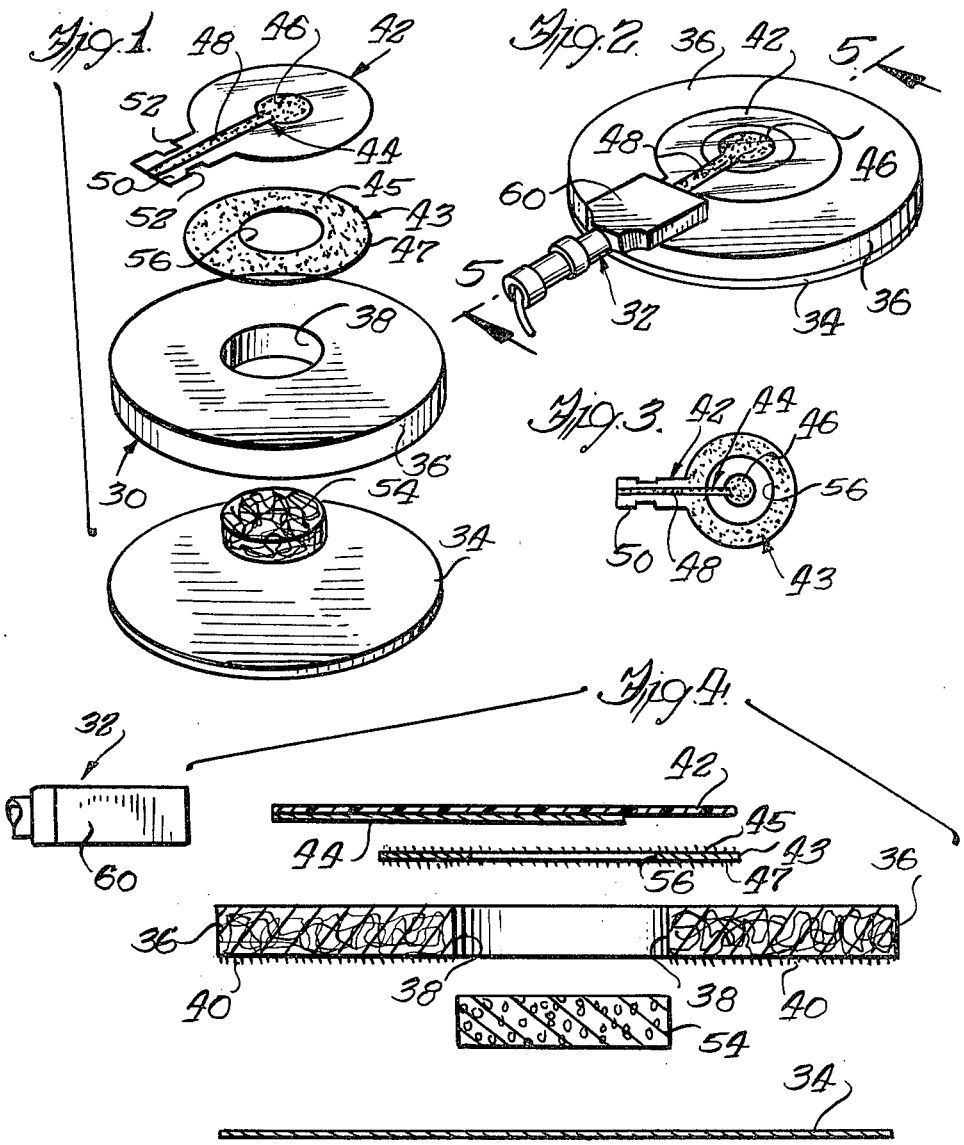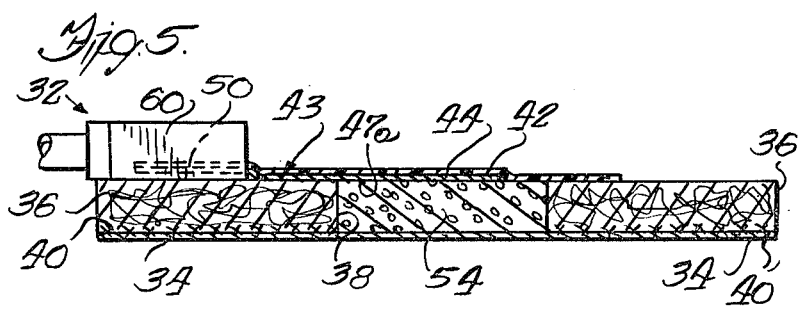

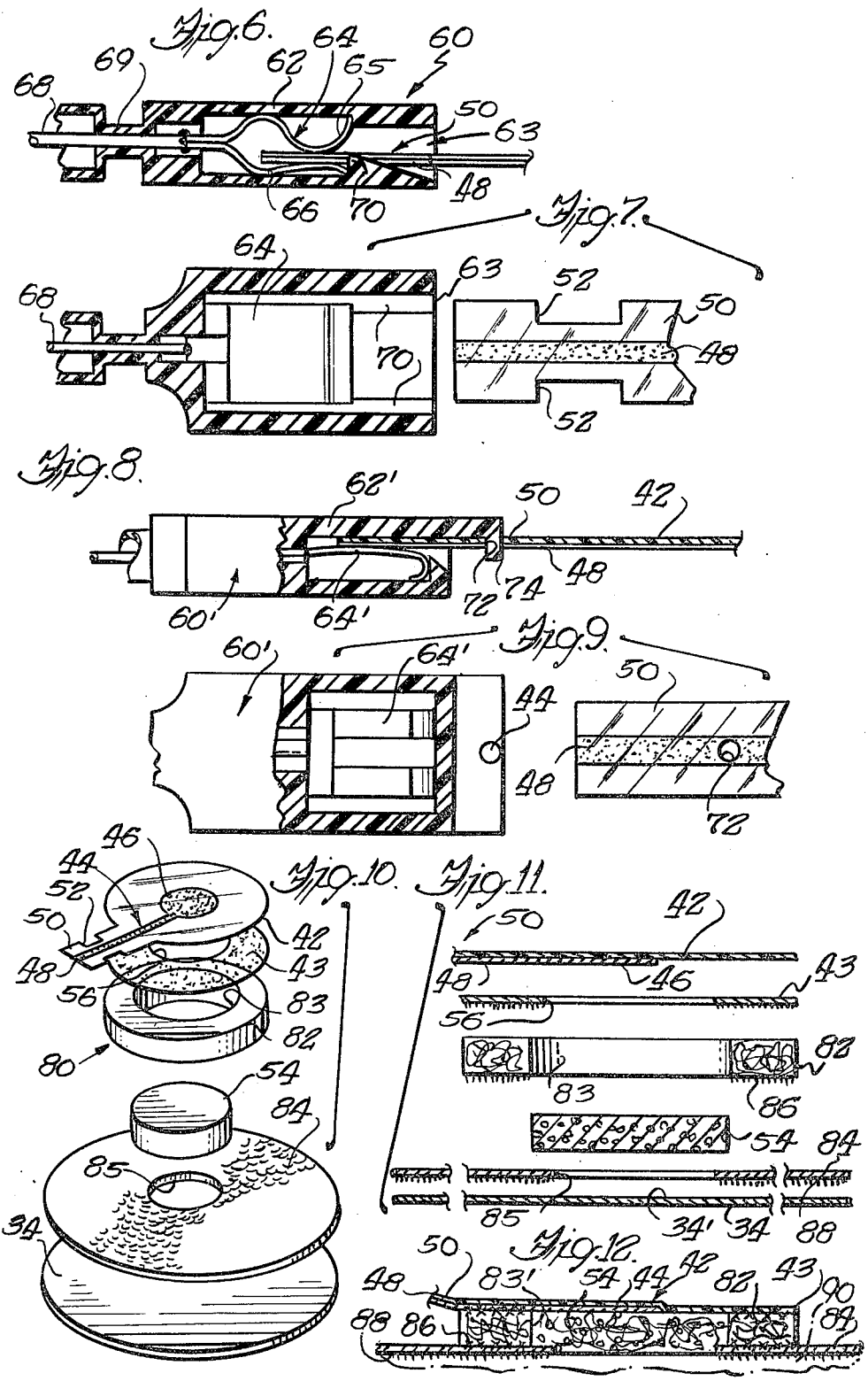

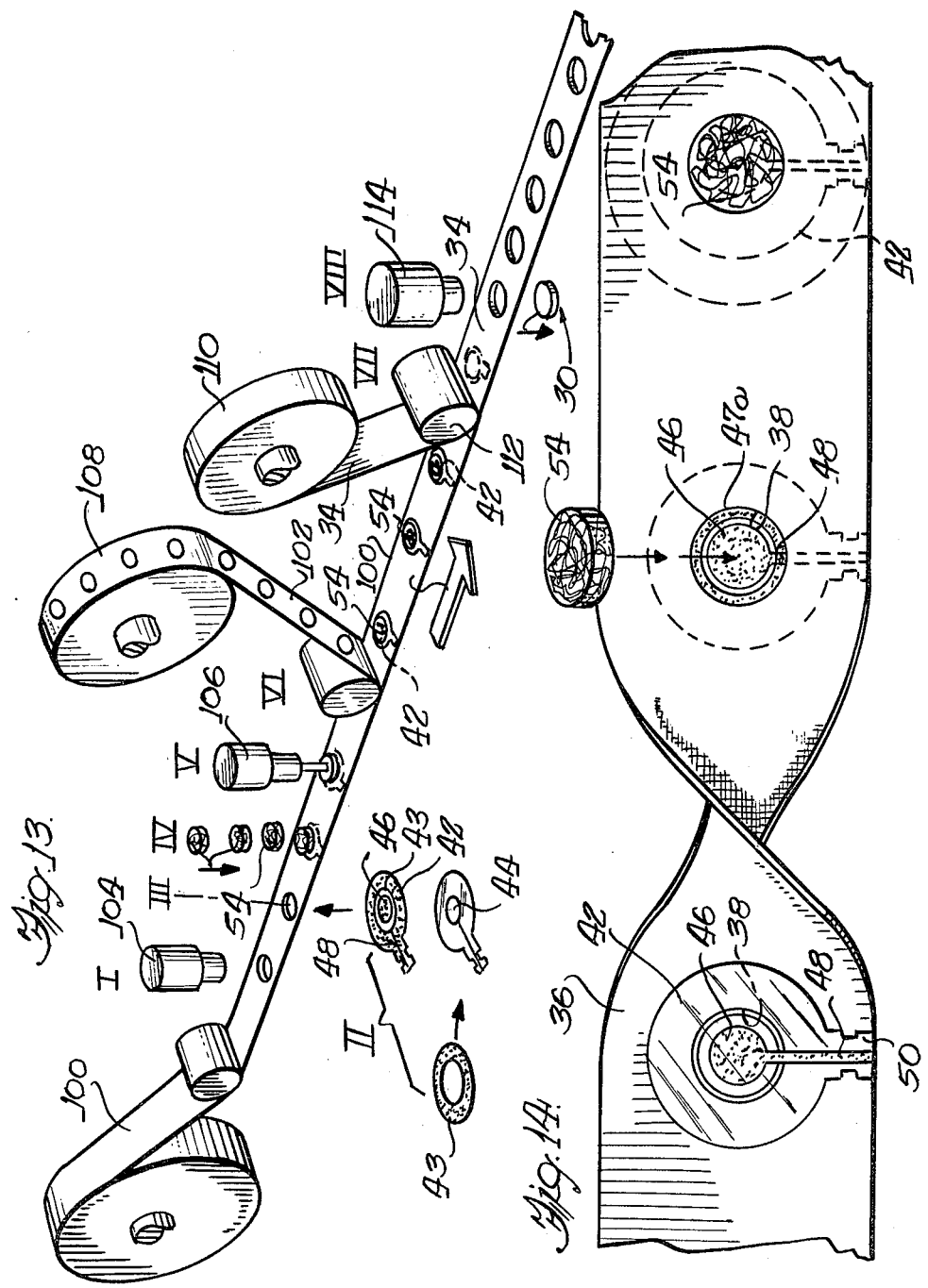

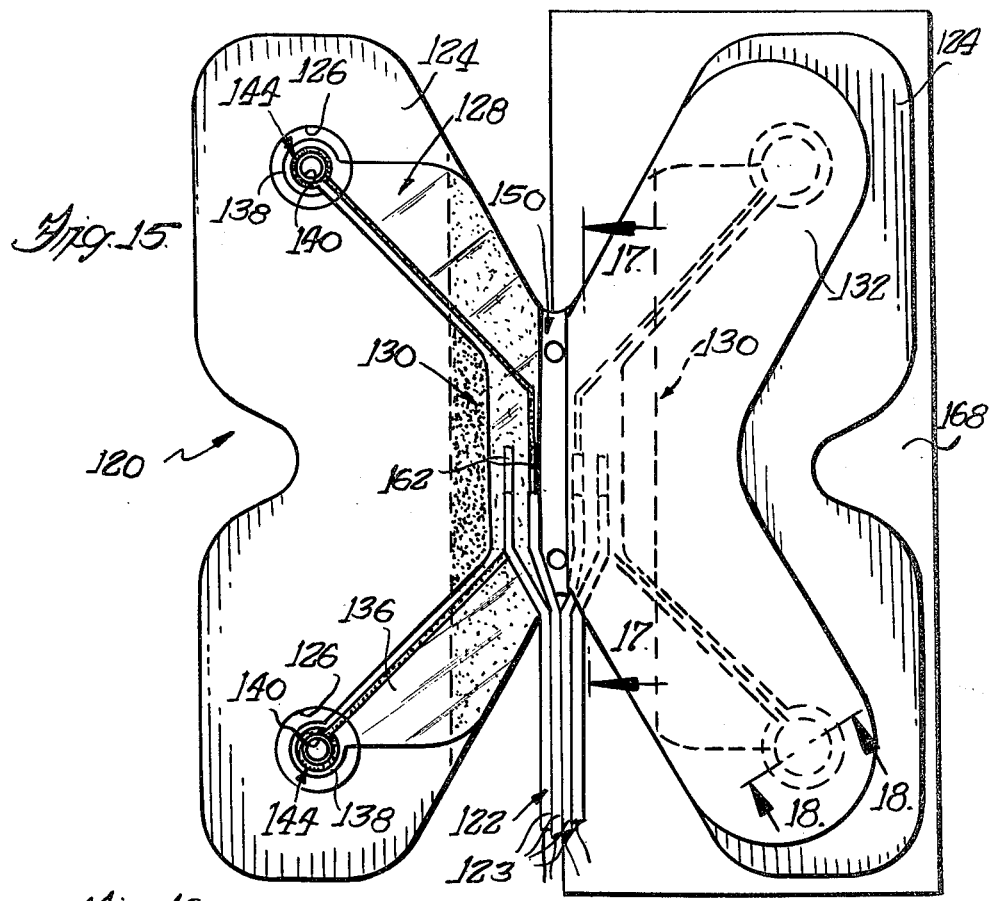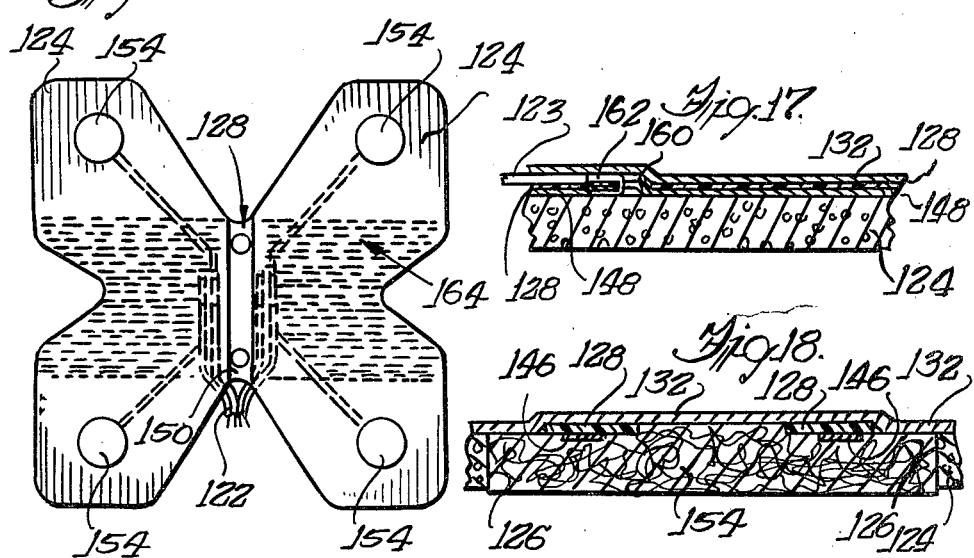

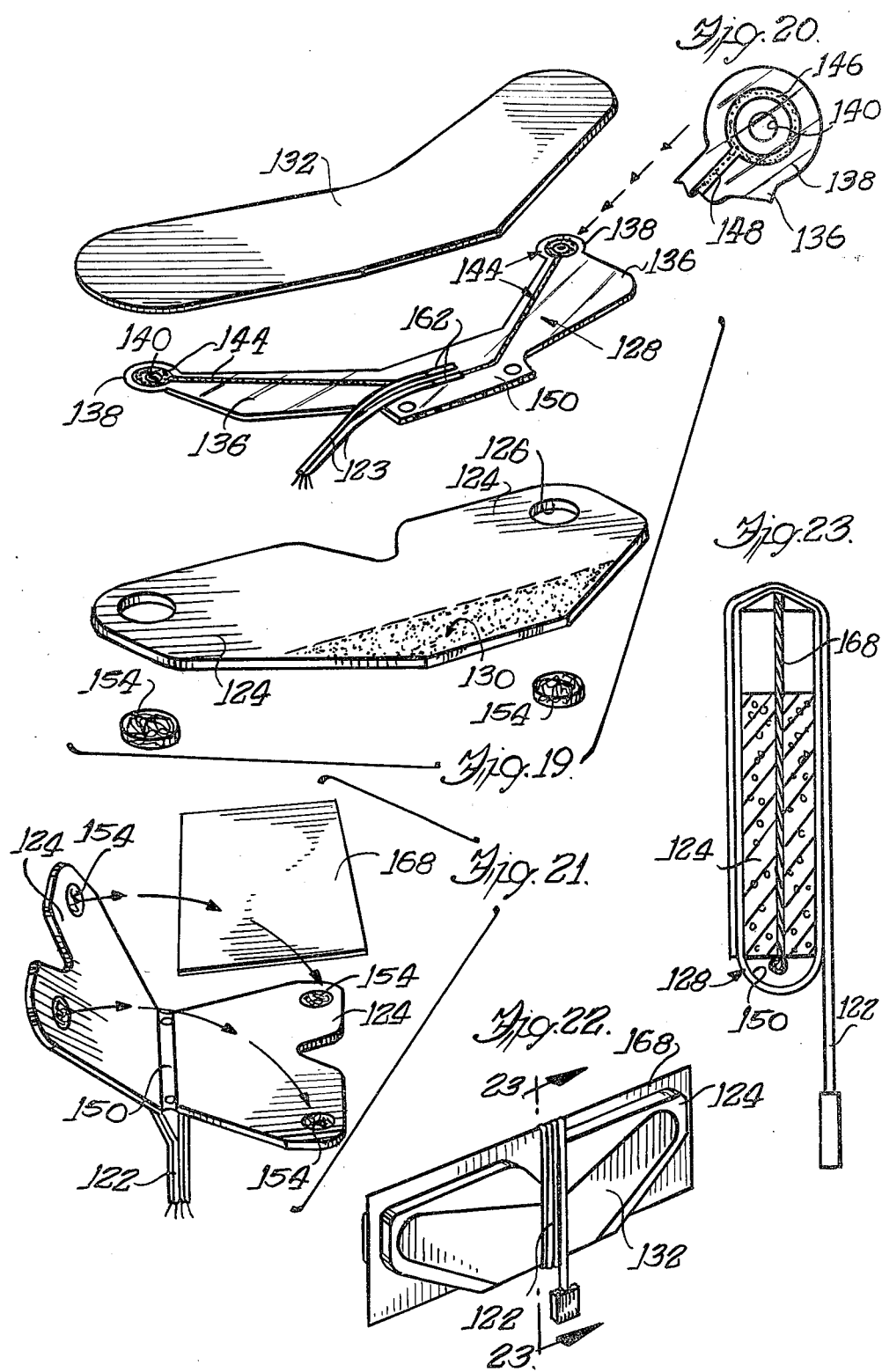

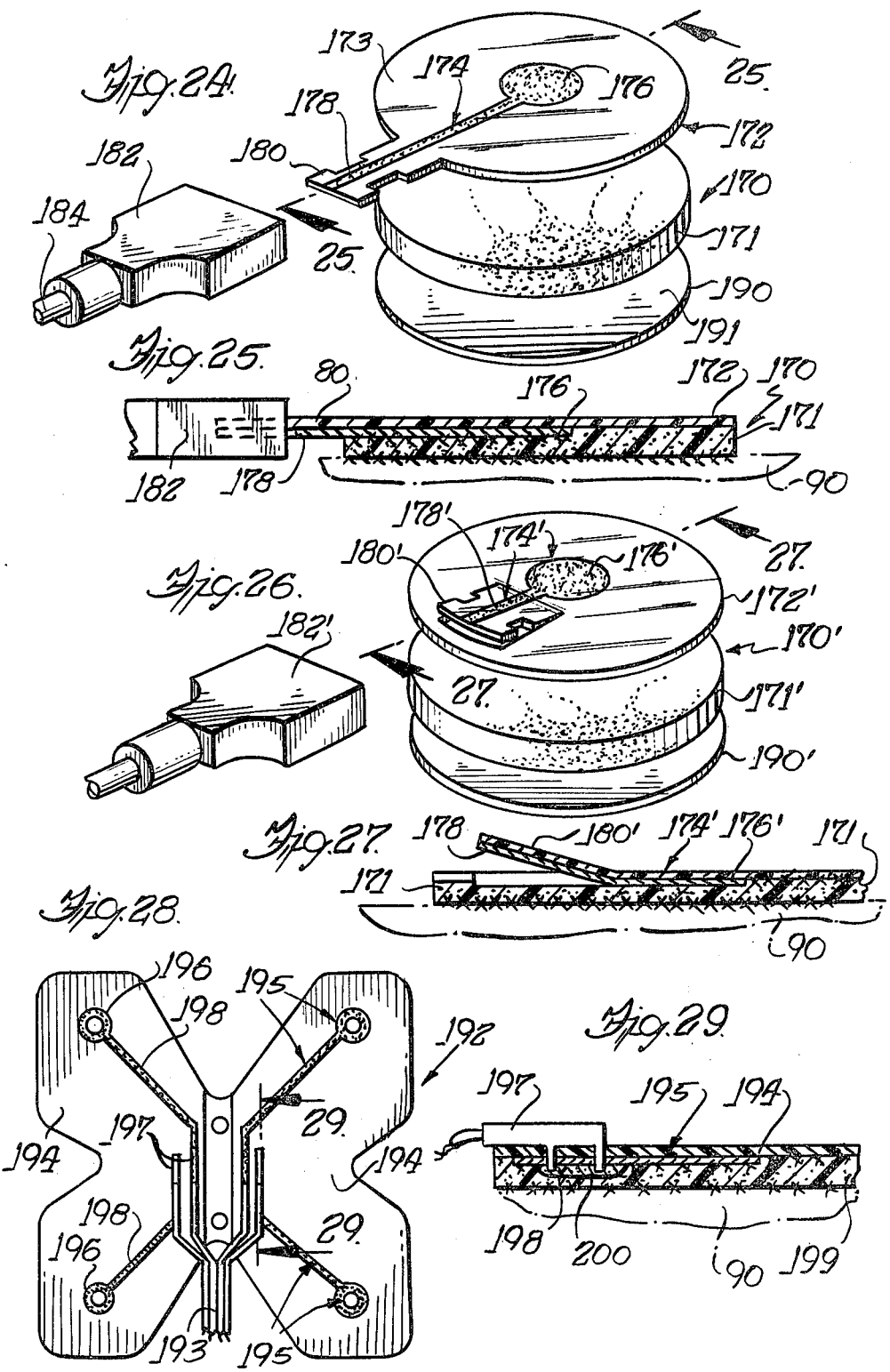

MEDICAL ELECTRODE CONSTRUCTION

BACKGROUND OF THE INVENTION

The present invention relates to electrodes, and more particularly to disposable medical electrodes of the type employed in the transcutaneous monitoring of biological or physiological electrical potential associated with muscular activity.

In recent years, medical science has developed the art of transcutaneous monitoring to a rather high degree and for a variety of purposes. This type of monitoring is used to detect muscular activity of the heart muscle by use of electrical apparatus referred to in the art as an electrocardiograph (ECG). The resulting traces or electrocardiograms achieved with this procedure provide a diagnostic tool which enables the cardiologist to detect heart disease and general defects, etc. In addition to cardiomuscular applications, transcutaneous monitoring can be employed to indicate the degree of nerve blockage resulting due to anesthetization of a patient during surgery. In this regard, one set of electrodes are used to apply a controlled, low voltage potential to a particular muscle nerve, and a second set of electrodes may be used to monitor the resulting muscular contractions. These contractions are recorded on a electromyograph (EMG), with the resulting trace indicating the degree of effectiveness being achieved with the anesthetic.

The electrodes initially developed for ECG or EMG applications were reusable, and referred to as "permanent electrodes". These electrodes were of a type which utilized a non-conductive base that was applied to the skin either by means of suction cups or straps, with a metal terminal element housed within the non-conductive base and connected to the ECG or EMG apparatus via lead wires. To assure proper electrical contact, an electrolytic gel or paste was often employed in conjunction with the metal terminal. In many of these early designs, the terminals employed were either pure silver, German silver (pewter) or silver-plated metals or plastics, as it was found that silver provided superior results due to its tendency not to store an electrical charge. As can be appreciated, these permanent electrodes were rather expensive to manufacture. Also, the permanent type of electrode required that it be cleaned and disinfected after each use and before reuse. This procedure was time consuming such that disposable or single use electrodes were soon developed which out of necessity had to be of an inexpensive construction. Examples of several types of disposable electrodes can be found in U.S. Pat. Nos. 3,989,035 and 3,805,769.

These disposable electrodes typically included a support structure for the metal terminal element in the form of a relatively thin adhesively coated layer or disc of cellular foam, or in some applications, a thin microporous tape is used. The requisite metal terminal was provided by the employment of a two piece snap fastener engaged either directly through the foam or tape layer, or in some instances, the support arrangement was apertured with a second layer of impervious material overlying the aperture, and the snap fastener carried by said second layer. In conjunction with the snap fastener, a porous matrix was applied which in the case of a pregelled electrode, was impregnated with a quantity of gel, and a cover arrangement of some sort placed over both the gelled matrix and the adhesively coated surface of the support arrangement.

The snap fasteners which provide the electrical terminals for these prior art electrodes have proven to be both expensive, and a source contributing to inconsistent performance of the electrode. In this regard, the snap fastener component associated with the gelled matrix is of a two part construction, with an inner element and an outer element, and is either totally or partially constructed of silver, stainless steel, nickel, or a silver-coated plastic or metal component. As such, the snap fastener is a relatively expensive component of the overall electrode construction, however, this design is tolerated as the snap fasteners lend themselves to the high speed automated construction of the electrode, necessary to achieve low cost production.

Further, it has been found that in use the snap fastener contributes significantly to the often erratic performance of the electrode. In this regard, the electrode is connected to the ECG apparatus by means of a lead wire having a female type snap connector on the end thereof engaged over the post or male component of the snap fastener. This connection provides considerable mass with respect to the remainder of electrode, such that patient movement results in alterations in the disposition of the electrode terminal with respect to the skin of the patient. More specifically, any movement producing tension in the lead wires would tend to pull the electrode terminal away from the patient's skin, whereas if the patient should happen to roll over, the protruding nature of the snap fastener would cause the metal terminal to be forced inwardly toward the skin, all of which contributing to the production of rather inconsistent ECG traces. As a further problem, electrodes with projecting snap fastener type terminal means do not lend themselves to stacking, and must be handled carefully during shipping and storage. In this regard, any rough handling or compressing together of the electrodes will tend to squeeze the gel from the gelled matrix.

The electrode system and electrode design of the present invention, as illustrated and described hereinafter, eliminates the need for the snap fastener as a component of the terminal means. Further, the present design achieves elimination of the snap fastener component, in a manner which results in improved performance, in that stability of the terminal position vis-a-vis the patient's skin is attained. Still further, this improved electrode design lends itself readily to automated assembly, and is usable with an overall system that envisions further improvements in the manner of connecting the electrode to the lead wire extending from the ECG or EMG apparatus.

More specifically, the electrode designs of the present invention utilizes a terminal arrangement provided by a pattern printed with conductive ink on a sheet of stable, semi-flexible, plastic-like material. The term "semi-flexible" is used with respect to the terminal bearing sheet for purposes of description, in that said sheet must be capable of slight flexure, yet must be relatively stiff or rigid, so as to resist any stretching or permanent deformation during use. Should stretching or deformation occur, this would result in fracture or interruption in the continuity of the printed conductive pattern, and thereby destroy its effectiveness as a conductive element. It has been found, that a relatively thin, clear, plastic-like film such as that sold under the trade name "MYLAR", is satisfactory for this purpose.

Looking to the overall basic construction, the electrode design of the present invention utilizes a support arrangement or layer which may be fabricated from a relatively thick, closed cell foam material of various types widely known in the trade, with one side of the foam support layer coated with a standard medical grade adhesive for securing or adhering the electrode to the skin of the patient. The support layer is apertured and the semi-flexible plastic-like terminal bearing sheet is affixed to the side of the support layer opposite that upon which the adhesive is applied. In this regard, the plastic-like sheet is positioned with the side having the conductive ink pattern thereon facing the support layer, with the terminal portion of said conductive ink pattern aligned with the associated aperture. Preferably, the conductive ink pattern also includes a conductor portion extending away from the area of the aperture, to which a lead wire is connected. The aperture in the support layer and the overlying plastic-like sheet material serve to define a well or chamber in which is disposed a porous or reticulated matrix, such as may be provided by a sponge-like plastic-like material, many versions of which are well known in the art. The porous matrix, or "gel pad" as it is often termed, is impregnated with a quantity of electrolytic gel, also of known formulation. A suitable easily removable cover arrangement overlies the adhesive coating on the support layer and the gel pad to prevent deterioration of the gel during storage.

The use of the semi-flexible terminal bearing sheet provides a relatively low mass terminal arrangement, which in use achieves a constant, stable positioning of the terminal means with respect to the skin of the patient. That is to say, the terminal portion will be spaced from the patient's skin, with the intermediate space filled by the electrolyte gel and the gel impregnated pad or matrix. This spacing is referred to in the art, and hereinafter, as the "gel column". More specifically, due to the low mass of the terminal arrangement provided by the conductive pattern on the sheet and the manner of connection of the electrode to the ECG apparatus, any patient motion, rolling over of the patient, or any tension on the ECG lead wires will not affect gel column stability to a great extent. Thus, the present design provides an inexpensive, disposable electrode capable of attainment of a consistent, highly accurate trace from the ECG apparatus.

As mentioned above, the manner of connecting the electrode to the ECG apparatus lead wire as contemplated by the present invention is also of significance, and contributes to the overall effectiveness of the electrode system. In both the single terminal and multi-terminal designs illustrated and to be discussed, the lead wires are connected at areas remote from the terminal portion. In one preferred, disclosed embodiment, the plastic-like, semi-flexible terminal bearing sheet includes a tab segment which is free of connection or adherence to the underlying support layer. The conductive pattern printed on said semi-flexible plastic-like sheet includes a conductor portion extending along this tab segment, such that the tab may be inserted within an electrical connector affixed to the end of an ECG lead wire. As will be discussed, the construction of the connector and the tab segment are such that they serve to isolate any stress or strain from the area of the terminal portion, which might affect the gel column.

A further aspect of the present invention and one most particularly applicable with respect to the single terminal electrode design discussed above, is the manner by which the design lends itself to automated fabrication. In and of itself, automated fabrication of an electrode is not novel, one such method of being illustrated and described in the aforementioned U.S. Pat. No. 3,805,769. The present invention, however, contemplates a novel method of assembly that is particularly advantageous with respect to the single terminal design as disclosed herein and other existing or possible future electrode designs.

In addition to the single terminal type of construction discussed above, the invention also contemplates various forms of multi-terminal assemblies, one of which is illustrated in the drawings and discussed in detail hereinafter. With the illustrated, contemplated design, a plastic-like, semi-flexible terminal bearing sheet is employed to join together two similar shaped support layers, each having one or more apertures therein with a terminal element on said sheet aligned with each aperture. With this arrangement, the semi-flexible sheet not only carries the terminal means, but acts as a hinge or connection between the respective support layer to provide an integral yet articulated assemblage. As will become apparent from the discussion to follow, this design is extremely advantageous with regard to both use of the multi-terminal assembly, its manufacture, and packaging thereof.

The present invention is possessed of numerous features and advantages, in addition to those discussed specifically above. It is believed that these features and advantages will become apparent from the detailed description of the invention which follows, taken in conjunction with the accompanying drawings which form a part of said description.

BRIEF DESCRIPTION OF THE DRAWINGS

FIG. 1 is an exploded perspective view of a single terminal electrode, including the cover member;

FIG. 2 is an assembled view of the electrode of FIG. 1, with a lead wire connector attached to the electrode assemblage;

FIG. 3 is a plan view of the semi-flexible, plastic-like terminal bearing sheet, with the adhesive layer applied thereto;

FIG. 4 is an exploded sectional view of the electrode of FIG. 3;

FIG. 5 is a sectional view taken along the line 5—5 of FIG. 3;

FIG. 6 is a partial sectional view of one form of connector arrangement to be employed with the electrode assemblage of FIGS. 1 and 2 and the electrode tab segment engaged therewith;

FIG. 7 is a longitudinal sectional view of the connector of FIG. 6 with the tab portion of the electrode disengaged;

FIG. 8 is a partial sectional view of an alternate form of connector to that as shown in FIG. 6;

FIG. 9 is a longitudinal, partial sectional view of the connector form of FIG. 8, with the tab segment of the electrode disengaged;

FIG. 10 is an exploded perspective view of an alternate form of electrode assemblage constructed in accordance with the invention;

FIG. 11 is an exploded sectional view of the electrode as illustrated in FIG. 10;

FIG. 12 is a sectional view of the electrode embodiment in FIG. 10 adhered to the skin of a patient;

FIG. 13 is a schematic, diagrammatic view illustrating the respective steps of a method of constructing the electrode assemblage of FIGS. 1-5;

FIG. 14 is a partial schematic view illustrating several of the steps in the method of assembly as illustrated in FIG. 13;

FIG. 15 is a plan view of a multi-terminal electrode, constructed in accordance with the present invention, with an upper foam layer removed from the left hand portion of the assemblage, as viewed;

FIG. 16 is a view of the adhesively coated surface of the electrode of FIG. 15, illustrating the reverse side of said electrode and the application of a deactivating compound to certain portions of said adhesively coated surface;

FIG. 17 is a partial sectional view of the connector portion of the electrode of FIG. 15, taken along the lines 17—17 of said FIG. 15;

FIG. 18 is a partial sectional view through one of the terminal portions and the gel pad of the electrode assemblage of FIG. 15 taken along the line 18—18;

FIG. 19 is a partial, exploded view of the electrode construction as illustrated in FIG. 15;

FIG. 20 is a partial plan view of an extension portion on the semi-flexible plastic sheet at which a terminal portion on the conductive ink pattern is shown;

FIG. 21 is a perspective view of the manner in which the electrode assemblage of FIG. 15 is prepared for packaging;

FIG. 22 is a perspective view illustrating the electrode assemblage in the pre-packaged construction;

FIG. 23 is a sectional view taken along the line 23—23 of FIG. 22;

FIG. 24 is an exploded perspective view of still another type or form of electrode design in accordance with the invention;

FIG. 25 is a sectional view along the line 25—25 of FIG. 24;

FIG. 26 is a perspective view similar to FIG. 24, and illustrating an alternate form of connection of the electrode to a lead wire;

FIG. 27 is a sectional view taken through a completed electrode of FIG. 26, generally along the line 26—26;

FIG. 28 is a plan view of a multi-terminal electrode constructed in accordance with the design of FIG. 24, and having pre-attached lead wires; and FIG. 29 is a sectional view taken along the line 29—29 of FIG. 28, and illustrating the crimp-type connection for the lead wires.

DETAILED DESCRIPTION OF THE DRAWINGS

The present invention is possessed of numerous aspects, and four distinct but related embodiments of electrode constructions are illustrated in the drawings. The first embodiment is encompassed by FIG. 1-9, and relates to a single terminal electrode assemblage designated generally 30 which is employed with a lead wire and connector assembly 32 and utilizes the relatively thick, foam type support arrangement or layer. FIGS. 10-12 illustrate an alternate form of a single terminal design 80 which is adapted for use with the assembly 32 (not shown in said figures). This alternate design 80 employs a support arrangement which is comprised of a relatively thick foam ring to provide the desired gel column, and a thinner, more extensive microporous layer, which microporous layer includes the adhesive material employed to affix the electrode to the skin of a patient. In FIGS. 13 and 14 there is shown rather schematically, a method of assemblage for the electrode construction 30 of FIGS. 1-5. A multi-terminal electrode construction in accordance with the present invention is shown in FIGS. 15-23, and designated generally 120. Still a further type of electrode construction is shown in FIGS. 24-29, wherein the support arrangement is provided by a conductive adhesive layer, thereby enabling elimination of the foam and/or microporous layers as well as the porous matrix. In the discussion that follows, even though common components of the various embodiments will be designated by similar terms, for purposes of description and understanding different reference characters will be utilized. As a further matter, since certain of the features of the various electrode designs are embodied in extremely thin layers or components, certain of these have been exaggerated dimensionally in the drawings in order to facilitate description and discussion.

Looking now to FIGS. 1-5, the construction of a single terminal electrode assemblage 30 is shown and will be considered in detail. In this regard, the term "electrode construction" is used collectively to indicate the assemblage as actually applied to the skin of a patient, as well as said assemblage in conjunction with a release liner type cover 34. More specifically, the electrode construction 30 includes a base or support arrangement 36 in the form of a layer of foam-like plastic material such as polyethylene foam which material is preferably of a non-reticulated or closed cellular construction to prevent absorption of the gel material. The base or support layer 36 includes a generally central aperture 38 extending completely through the layer 36. One surface of the support arrangement provided by the foam layer 36 includes a coating 40 of an adhesive material (FIGS. 4 and 5), which adhesive material may be any of a number of commercially available medical grade adhesives presently in use with prior art types of electrodes, and thereby well known in the art.

Affixed to the surface of the support layer 36 approximate said adhesively coated surface is a sheet of semi-flexible plastic-like material 42 which is secured in overlying relation with respect to the aperture 38 by means of an extremely thin ring-like component or layer 43 having adhesively coated surfaces 45 and 47 on opposite sides thereof; said component being termed hereinafter "a double sided adhesively coated annulus". The assemblage of the sheet of plastic-like material 42 to the support layer 36 in effect closes one end of the aperture 38 and serves to cooperate therewith to define a well or chamber 38' for a purpose to be discussed. The sheet 42 is referred to as constructed of a "semi-flexible, plastic-like material" for purposes of description and general definition. In this regard, it is to be understood that there exists numerous types of materials from which the sheet 42 can be constructed; these materials, however, must possess certain properties in that is important that they are relatively thin and slightly flexible, yet they must not be subject to stretching or permanent deformation during normal use or during assembly. A material which has proven satisfactory for use in construction of the sheet 42 is a clear plastic material sold in sheet form under the trademark "MYLAR".

Further, the semi-flexible, plastic-like sheet 42 has terminal means thereon in the form of a conductive ink pattern 44 printed directly on one surface of said sheet. Due to the clear nature of the preferred material for the semi-flexible sheet 42, this pattern is visible from the opposite surface of said sheet. The pattern 44 of the disclosed embodiment 30 includes a generally circular terminal portion 46 and a conductor portion 48. As can best be seen in FIG. 1, the conductor portion 48 extends from the terminal portion 46 along a tab segment 50 of said sheet 42, which tab segment includes a pair of notches 52 for the purpose to be discussed.

Disposed in the well 38' is a porous matrix or gel pad 54, preferably formed of an open cellular sponge like plastic material. Keeping in mind the fact that the electrode 30 is of the pregelled type, there is also included a quantity of electrolytic gel (no reference character), which impregnates the matrix 54 and effectively fills the well 38' provided by the aperture 38. This electrolytic gel can be any of various commercially available products, as for example sodium chloride in agar. In the event that the electrode is not to be pregelled, the employment of said electrolytic gel may be dispensed with, without variation in the overall construction.

With reference to FIGS. 3, 4 and 5, it should be noted that the double sided adhesive annulus 43 includes an aperture 56 which is smaller in diameter than the aperture 38 in foam layer 36, and upon assembly, surrounds the terminal portion 46 without overlying said terminal portion, FIG. 3. As such, when the semi-flexible sheet 42 is mounted to the support arrangement, 36, a portion 47a of the adhesive coating 47 on said ring 43 is exposed interiorly of the aperture 38, as best seen in FIG. 3. Thus, upon disposition of the gel matrix 54 in the aperture 38, as shown in FIG. 5, said matrix 54 is adhered to the semi-flexible plastic-like sheet 42 by means of the exposed adhesive portion 47a.

To complete the electrode construction 30, the cover 34 is applied to the adhesively coated surface 40 of the foam layer 36, said cover 34 overlying said surface 40, as well as the gelled matrix 54. The cover 34 is preferably constructed of a high density polyethylene having a release coating on the surface thereof engaged against the adhesively coated surface 40 of the foam layer 36. As such, when it is desired to utilize the electrode, the cover 34 can be removed easily and the electrode construction applied to the skin of the patient, with the adhesive surface 40 providing the means for affixing and maintaining the electrode in proper position.

Returning to the semi-flexible sheet 42 with the conductive ink pattern 42 thereon, the ink utilized is applied by conventional printing techniques in an extremely thin layer. 0.001-0.010". As such, patterns other than the pattern 44 as specifically illustrated may be easily employed. Ink of the general type contemplated is comprised of a composition of a conductive metal, carried within a binder. It is preferred that the ink utilized employ silver as the conductive component. Ink of this nature can be obtained from numerous sources, one such source being E. I. DuPont DeNemours and Company. The particular compositions available from this company include silver in a proprietary binder system specifically designed to adhere to a plastic-like material such as "MYLAR" without peeling or cracking during flexure of said material. As such, it can be appreciated that the material used for the plastic-like sheet or substrate 42 must be sufficiently rigid to resist any stretching or deformation during normal use or assembly. Should stretching occur, the danger exists that the ink pattern will be fractured, destroying its continuity and the ability of said conductive pattern 44 to function as an electrical terminal arrangement. As an additional matter it is also preferred that the surface of the terminal portion 46 of said conductive silver ink pattern be chlorided to produce a thin silver chloride coating, which has proven to provide superior performance. This process of chloriding can be accomplished in any one of several known manners, such as electrodeposition or by reaction with chlorine gas.

An additional feature of the invention that should be noted, is the construction of the sheet 42 with its tab portion 50, and the location of the adhesively coated annulus 43 thereon, as best seen in FIG. 3. In this regard, the sheet 42 is fabricated and the conductive ink pattern 44 is printed thereon prior to application of the adhesive annulus 43. The adhesive annulus 43 includes an aperture 56, such that upon its application to a surface of the semi-flexible sheet 42, it will encompass the terminal portion 46 of the conductive ink pattern 44, but preferably does not cover or overlie said terminal portion 46. As shown in FIG. 3, the adhesively coated annulus extends only to the general periphery of the main segment of the sheet 42, and does not extend along the tap segment 50, thus overlying only partially the conductor portion 48. When the sheet 42 is assembled to the support layer 36 only the main segment thereof is adhered to the upper surface of said support layer 36, the tab segment 50 remaining free and unsecured thereto. In addition to providing the surface 47a to which the porous matrix 54 is attached, and securing the sheet 42 to the support layer 36, the annulus 43 also serves to seal the gel matrix chamber 38' and prevent migration or leakage of the gel along the tab segment 50. As such, taking into account the non-porous nature of the foam layer 36, the sheet 42 and the release liner 34, it can be seen that there is provided a substantially hermetically sealed chamber 38' for the gel which serves to resist deterioration and drying out of the gel during storage prior to use.

The free or unsecured nature of the tab segment 50 enables the electrode to be connected to ECG apparatus by means of a lead wire arrangement 32 having an electrical connector 60. As seen in FIGS. 2 and 5, the tab segment 50 is engaged with or received within the electrical connector 60 and a connection is made with the conductor portion 48 on said tab segment 50. Details of two preferred or anticipated designs for connectors 60 are illustrated in FIGS. 6-9 and will be discussed more fully hereinafter. While these specific designs are believed to be novel per se, it is also believed that the general concept utilizing a free tab segment and a printed ink conductor segment thereon to achieve electrical connection with the lead wire arrangement 32 is a novel concept.

Looking to FIGS. 6 and 7, there is illustrated a first form or type of electrode connector 60 which may be employed in the electrode system of the present invention. The connector 60 includes a housing 62 having an open end 63 leading to the interior thereof, wherein there is mounted a spring-type clip terminal 64 having upper and lower arms 65 and 66, respectively. A lead wire 68 passes inwardly of the housing with the housing being crimped to engage said lead wire at 69, said wire 68 being connected to the terminal 64. At the forward entry portion of the open end of the housing 62 there is provided a pair of spaced, ramp shaped projections 70. The projections 70 are sized and spaced apart such that upon disposition of the tab segment 50 within the housing, the projections 70 will be received within the notches 52 of said tab segment. The tab segment 50 is received between the spring-like arms 65 and 66 with the upper spring arm 65 forcing the tab segment downwardly to maintain the tab segment engaged over the projections 70. Accordingly, if any tension is applied to the lead wire 68, the engagement of the projections 70 in the notches 52 will serve to resist inadvertent disconnection, and also function to achieve a degree of strain relief, isolating any stress from the area of the electrode terminal portion 46. It can be appreciated further, the metal terminal 64 is designed to engage the printed ink conductor portion 48 on the tab segment 50, thereby effecting an electrical connection. Further, since said metal terminal 64 includes a pair of opposed arms 65 and 66, inverting of the connector 60 upon assembly would not preclude attainment of a proper electrical connection.

FIGS. 8 and 9 illustrate a modified type of connector 60' for use with a tab segment 50 having an aperture 72 formed thereon. In this regard, the connector housing 62' has a projection or post 74 formed thereon, and sized for disposition in said aperture 72. Accordingly, in the assembled or engaged position, as shown in FIG. 8, the spring terminal 64' will engage the printed ink conductor portion 48 to effect the desired electrical connection, and also maintain the tab segment 50 engaged over the post 74.

A modified form of electrode construction in accordance with the present invention is illustrated in FIGS. 10-12, and designated generally 80. The electrode embodiment 80 differs from the electrode construction 30 in that the support arrangement includes a relatively thick ring 82 which may be made of a foam material or a rigid plastic, and a section of microporous tape material 84 having an adhesive coating 86 on one surface thereof for adhering the electrode to the skin of a patient. The ring 82 includes a central aperture 83, while the section of microporous tape 84 has an aperture 85 of a somewhat smaller dimension, for a purpose to be discussed more fully hereinafter. In certain applications where an electrode will be in place for an extended period of time, use of a microporous tape layer prevents dermatalogical problems as it allows air to reach the patient's skin surface. Suitable types of medical grade of microporous tape are available and well known in the art, one being sold under the trade name "MICROPORE" by the 3M Company, and another by Johnson & Johnson under the trademark "DERMICIL".

The remaining construction of the electrode 80 is somewhat similar to that of the electrode 30 discussed above, in that the terminal arrangement is provided by a semi-flexible plastic-like sheet 42 of identical construction to that previously detailed, said sheet including a tab portion 50, a pattern 44 printed thereon with the conductive ink and defining a terminal portion 46 and a conductor portion 48. A double-sided adhesive annulus 43 is used to affix the semi-flexible sheet 42 to the upper surface of the ring 82, with the tab 50 remaining free of any connection thereto. The lower surface of the ring 82 as mentioned previously, includes an adhesive layer 86, which affixes the ring 82 to the upper surface of the micro-porous disc 84. The application of the semi-flexible plastic-like sheet 42 to the ring 82 serves to define a well 83' in which a porous matrix 54 is disposed. As was the case with the electrode 30, the double-sided adhesive annulus 43 has a central aperture somewhat smaller than the aperture 83 of the ring, such that a portion of the adhesive will be exposed with the porous matrix 54 secured thereto. A cover member 34 is provided, having an upper surface 34' upon which there is provided a release liner coating which enables the cover 34 to be removed easily immediately prior to application of the electrode to the skin of a patient.

In FIG. 12, the assembled electrode construction 80 is shown mounted to the skin 90 of a patient. It can be seen that the relatively thick ring 82 serves to provide a substantial well 83' for the gel pad 54, which also defines the height of the gel column. Further, it should be noted that the aperture 85 in the microporous support arrangement component 84 is of slightly smaller dimension than the gel matrix 54, so as to overlap slightly said matrix in the assembled condition. This overlapping design serves to further retain the gel matrix 54 in position, and prevent migration of the gel along the interface with the patient's skin 90.

Attention is now invited to FIGS. 13 and 14, wherein a preferred method of manufacture of the electrode construction 30 is shown, the illustration therein depicting the successive steps of said methods in somewhat schematic fashion. Initially, an elongate strip 100 of foam material 36 in roll form is provided, with said strip 100 having a first release liner 102 covering the adhesive surfaces 40 thereon. The strip material 100 is oriented for feeding to a first station I with the release liner 102 facing upwardly. At the station I the apertures 38 are formed in the strip 100 by a die or punch 104 at spaced successive locations along the strip. At a separate substation II, the double-sided adhesively coated annulus or ring 43 is applied to the sheet of semi-flexible plastic-like material 42, to attain a preassembled component as was illustrated and discussed with respect to FIG. 3. Prior to the application of the annulus 43, to the semi-flexible sheet 42, the printed ink conductor pattern 44 is applied to a section of plastic-like sheet material by a conventional printing process (not shown) and the sheet material die cut or otherwise formed to the desired shape for the sheet 42.

Next, the preassembled terminal bearing sheet 42 and adhesive annulus 43 are affixed to the undersurface of the strip 100 at station III. With reference to FIG. 14, the resulting assembly is illustrated in the left hand portion of said FIG. 14, as viewed, which illustrates the lower surface of the strip 100 at station III. In this regard, it can be seen that the semi-flexible clear sheet 42 is positioned such that the terminal portion 46 of the conductive pattern 44 is aligned with the aperture 38. Looking now to the central portion of FIG. 14, the strip 100 has been rotated 180°, such that the upper surface carrying the first release liner 102 is the facing surface. It can be seen that a portion 47a of the adhesive annulus 43 extends inwardly of the aperture 38 and is disposed in surrounding relationship to the terminal portion 46. This is the condition of the partially assembled electrode construction, as it is presented to station IV.

At station IV, a precut porous matrix 54 is supplied and disposed within the aperture 38, this results in the matrix adhering to the adhesive portion of 47a. This step is also illustrated in the central portion of FIG. 14.

The strip 100 next passes to the station V, wherein a quantity of electrolytic gel is injected into said matrix, which gel impregnates the matrix 54 and fills the well 38'. In this regard, a dispenser 106 will meter out a pre-determined quantity of the gel to prevent over filling of the gel chamber.

The strip 100 then passes to station VI, at which the apertured, first release liner 102 is removed and discarded as waste. As can be seen, the apertured release liner 102 is coiled for easy disposition, as illustrated 108. The strip 100 with the partially assembled electrode thereon next passes to the station VII, at which a second release liner 34 is applied. The second release liner 34 is preferably a high density polyethylene sheet with a release liner coating 34' thereon, which material ultimately forms the cover for the pregelled electrode 30. In this regard, the second release liner material 34 is in roll form 110, and is applied to the strip 100 by a roller 112.

As the strip 100 passes from the station VII, the basic construction for the electrode 30 is complete. At station VIII, a die cutter or punch 114 severs the completed electrode construction 30 from the strip 100. The remaining portion of the strip 100 thus becomes waste and can be easily discarded, as the adhesively coated surfaces thereon remains covered by the waste portion of the release liner 34.

Looking to FIGS. 15-23, there is illustrated a multi-terminal electrode, designated generally 120, and constructed in accordance with the present invention. Multi-terminal electrode constructions of this nature are often referred to in the art as "back pads", in that they are affixed to the patient's back to provide monitoring during chest or abdominal surgery and during recovery thereafter, wherein it would be impractical to utilize chest mounted electrodes. Accordingly, while the multi-terminal electrode illustrated is of the "back pad" type, it is to be kept in mind that other types of multi-terminal electrodes such as used in muscle stimulation, electromyographic monitoring or pain therapy may also be constructed in accordance with this invention; as such with respect to multi-terminal designs, the embodiment of FIG. 15 to be discussed is merely illustrative of one preferred type, and the invention is not limited thereto.

Looking now to FIGS. 15 and 19, the multi-terminal electrode construction 120 contemplates employment of a preconnected lead wire arrangement 122, including a plurality of separate lead wires 123. A further point to be kept in mind for better understanding of the discussion to follow, is that the electrode 120 as shown in FIG. 15 has a sheet-like component or layer removed from the left-hand portion as viewed for purposes of illustration.

More specifically, the electrode 122 is comprised of a support arrangement provided by a pair of similarly shaped sections of relatively thick foam material 124. As was the case with the previously discussed electrodes, employment of a closed cellular type foam is preferred, however, any one of a number of various commercially available foam materials may be utilized. Each section of foam material 124 includes a pair of spaced apertures 126 formed therein. A singular section or sheet of semi-flexible, plastic-like material 128 is provided, said sheet being mounted to each of the foam sections 124 and in effect interconnecting said sections 124 by bridging the space or joint therebetween. The semi-flexible sheet 128 is preferably constructed of a plastic-like material of the same type as discussed with respect to electrodes 30 and 80, that is the term being "semi-flexible" being used to designate a type of material, such as "MYLAR", which will flex slightly, but will not stretch or permanently deform during normal use, assembly or storage. Said semi-flexible plastic-like sheet 128 which will be discussed in greater detail hereinafter, is initially affixed to the foam sections 124 by a partial adhesive coating on the upper surfaces of the foam sections 124 in the areas 130, as indicated. To complete mounting of the sheet 128, a second relatively thin foam layer or sheet 132 is employed which has an adhesive coating on the under surface thereof. Upon assembly of said second sheet 132, as illustrated in the right hand portion of FIG. 15, said sheet 132 overlies the semi-flexible plastic-like sheet 128 and is secured to both said sheet 128 and the upper surface of the foam layer 124 by said adhesive coating. It should be noted that while it is preferred that the layer or sheet 132 be of a foam or cellular material, other suitable materials may be employed.

The specific construction of the semi-flexible, plastic-like section or sheet 128 will now be considered. In this regard, the sheet 128 will be discussed primarily with the left hand portion of FIG. 15 and FIG. 19, it being understood that the right hand portion of said sheet is essentially identical, being a mirror image of that as illustrated. Further, with regard to FIG. 19, which is an exploded view of the electrode construction 120, the left hand portion of said sheet 128 can be viewed in somewhat greater detail.

The sheet 128 includes a plurality of arm sections or extensions 136 eminating from a base or central section 150, each of which terminates in generally circular portion 138. Each of the respective circular portions 138 includes an aperture 140 formed therein, as is best illustrated in FIG. 20. A plurality of individual terminal means corresponding in number to the apertures 126 in the sheet 124 are provided on the semi-flexible sheet 128. The terminal means in the preferred form of the invention are provided by four individual patterns 144, printed on the underside of the semi-flexible sheet 128 with a conductive ink of the same general type and in the same manner as discussed previously. Each pattern 144 includes a terminal portion 146 and an elongate conductor portion 148. As best shown in FIG. 20, the terminal portion 146 of the illustrated embodiment is of a ring-like configuration, encircling the aperture 140, with the conductor portion 148 extending along the arm or extension 136. The respective conductor portions 148 on each half of the sheet 136 extend in opposite directions, and terminate adjacent to each other on the base or central segment 150 of said sheet. The lead wire arrangement 122 is affixed to the base segment 150 and electrical contact with the conductor portions 148 is attained in a manner which will be discussed more fully hereinafter with respect to FIG. 17.

Completing the basic electrode construction 120 are a plurality of porous matrix members 154 which are engaged in the apertures 126, as best shown in FIG. 18. With reference to said FIG. 18 and also FIG. 15, it should be noted that the circular end portion 138 on the respective extensions 136 are of a diameter slightly less than that of the openings 126. Accordingly, when the semi-flexible plastic-like sheet 128 is mounted in position as shown in FIG. 15, the circular end segments 138 overlie the apertures 126 only partially. Further, taking into account the presence of the opening 140 in said circular end portions 138, it can be appreciated that when the second, relatively thin sheet of foam material 132 is applied over the semi-flexible plastic-like sheet 128, portions of the adhesive coating on said sheet 138 remained exposed, interiorly of the aperture 126. Thus, upon disposition of the matrix 154 with the aperture 126, said matrix will be adhered to the exposed adhesive portions, as is shown in FIG. 18. Thus, the respective matrixes are maintained in operative association with the terminal portions 146 carried on the circular end segments 138 of the projection 136.

Directing attention to FIG. 17, the manner of connecting the lead wire arrangement 122 to the semi-flexible plastic-like sheet 128 is illustrated. In this regard, a suitable crimp-type terminal connector 162 is included on the ends of the individual lead wires 123, the crimp-type terminal being engaged through the upper surface of the semi-flexible plastic-like sheet 120 at location 160, and bent over to effect firm electrical contact with the conductor portion 148 on the under surface of said sheet. The relatively thin foam like sheet 132 is engaged over the terminal connections 162, and is adhered in firm engagement to the plastic-like sheet about the area of said terminal connection 162, such that the engagement of said sheet with the terminal connection and its associated lead wire 123 serve to provide a measure of strained relief. As such any tension applied to the lead wires 123 will be taken up, at least partially, by the engagement of the flexible sheet 132 with the lead wire 123.

In FIG. 16, the under surface of the electrode 120 is shown with said electrode in the fully open condition. In this regard, the under surface of the respective support layers or sheets 124 is coated with a conventional medical grade adhesive for attachment of the electrode to the skin of the patient. Since the extent of the adhesive on the under surface is rather large, and further since it is not always desirable nor necessary to have the entire surface area of the electrode in adhesive contact with a patient's skin, a portion of adhesive is deactivated to avoid dermatological problems which may occur after extended periods of use of the electrode or back pad 120. In this regard, a medical grade silicone coating, as designated generally 164, is applied to the central area of each of support arrangement 124, as indicated. This coating in effect deactivates the adhesive in said central area, with the adhesive on the remaining portion, the areas surrounding the apertures 126 and gel pads 154, remain active and capable of effecting attachment of the electrode.

As was mentioned previously, the support arrangement for the preferred design utilizes a pair of separate, similarly shaped sheet sections 124, maintained in assembly by their joint connection to the plastic like sheet 128. This arrangement is for a specific purpose which will be discussed; however, it should be kept in mind that the present invention also envisions use of but a single support arrangement wherein the respective halves are provided by a single layer or sheet of foam material. The purpose for use of the arrangement wherein the semi-flexible plastic-like sheet 128 interconnects the respective layers 124 is to attain flexibility. More specifically, it can be appreciated that these back pads are rather extensive. Accordingly, with the disclosed arrangement, the central portion 150 of the plastic-like sheet 128 provides a hinge which permits the respective halves of the electrode to flex and adjust to the contour of the patient's back. Also, as will be apparent in conjunction with the discussion to follow with regard to FIGS. 21-23, this flexibility facilitates packaging of the electrode 120.

Looking first to FIG. 21, the manner for packaging or completing the electrode arrangement for storage is shown. As mentioned above, the semi-flexible plastic-like sheet 128 provides a hinge between the respective foam sections 124 of the support arrangement. This hinge area, the central segment 150 of the sheet 128, does not include portions of the conductive pattern 144 providing the terminal means. Accordingly, the respective foam layers 124 may be folded over upon themselves, as is indicated in FIG. 21, without undue flexing of the pattern 144. In this regard, a sheet of release liner material 168 is disposed intermediate the respective halves of the electrode, said sheet 168 having a release coating on both sides thereof. As such, the respective halves or sections 124 of the electrode are releasably secured against said sheet 168 in overlapped relation, as is best illustrated in FIGS. 22 and 23, with the lead wire arrangement 122 coiled as illustrated. As such, there is provided a compact arrangement for packaging and storage purposes.

In FIGS. 24-29, a still further modified version of the present invention is illustrated. In FIGS. 24-27 there is shown two forms of a single terminal electrode construction, designated 170 and 170' respectively. In FIGS. 28 and 29, there is shown a multi-terminal electrode construction using the general concept as to be discussed with respect to the single terminal electrodes 170 and 170'.

Looking first to FIGS. 24 and 25, the electrode 170 differs from the electrode 30, previously discussed, primarily in that the foam layer 36 and the gelled matrix 54 have been replaced by a specially constructed conductive adhesive layer 171. More specifically, the electrode 170 of FIG. 24 is illustrated in exploded fashion with the assembled arrangement being shown in FIG. 25, affixed to a patient. The electrode 170 is comprised of a sheet of semi-flexible plastic-like material 172 upon which is printed a conductive pattern 174. The pattern 174 preferably is formed with a silver ink, or some other type of conductive ink printed directly on the sheet material as discussed previously, and said pattern 144 includes a terminal portion 176, and a conductor portion 178. The semi-flexible plastic-like sheet 172 also includes the tab segment 180 adapted to be received within a connector 182 affixed to the end of a lead wire 184 in a manner similar to that as discussed with respect to the electrode of FIGS. 1-5. It should be noted that the conductor portion 178 extends along the length of the tab 180, which in turn extends from the periphery of the main segment of the electrode, which conductor portion 178 will be associated in electrical contact with a metal terminal housed within the connector 182.

The layer of conductive adhesive is affixed to the major or main segment 173 of the semi-flexible plastic-like sheet 172, but does not extend along the tab 180, whereby said tab remains free for engagement within a connector 182. A cover member 190, having a release liner coated surface 191 is provided, which is releasably attached to the under surface of the adhesive layer 171, and can be peeled off or removed for mounting of the electrode to the skin 90 of a patient, as is shown in FIG. 25.

Due to the conductive properties of the adhesive layer 171, the gel pad or matrix and foam support layer used with the electrodes discussed previously, are not required. As such, the conductive adhesive layer 171 is not apertured, as was the adhesive annulus 43 discussed previously, and overlies the terminal portion 176.

The adhesive layer 171 may be provided by any one of several known electrically conductive adhesives. One such conductive adhesive is produced by Johnson & Johnson Company under the trade name "BIO-HESIVE", and is disclosed in U.S. Pat. No. 4,066,078, which in turn references a pending U.S. application Ser.

No. 509,207, filed Sept. 25, 1974 and entitled "Hydrophilic Random Interpolymer Compositions and Method for Making Same". Other conductive adhesives and methods for rendering adhesive materials conductive are known in the art; as for example in U.S. Pat. Nos. 4,008,721; 3,998,215; 3,993,049; and 3,911,906. The aforesaid patents disclosed that certain adhesive compositions may be rendered conductive by a number of methods, including the dispersing of conductive materials such as conductive salts or metals throughout the composition. The adhesive layer 171 of the present invention is preferably constructed of a hydrophilic adhesive composition manufactured by Tyndale-Plain-Hunter, Ltd., which material may be rendered conductive by any one of the above noted methods, or other methods known in the art. This hydrophilic material is disclosed fully in U.S. Pat. Nos. 3,822,238; 4,156,066; and 4,156,067. Basically, the adhesive layer 171 is of a double sided nature so that it has one surface secured to the semi-flexible plastic-like sheet 172 and an opposed surface for attachment to the skin of a patient.

It can be appreciated that the elimination of the foam layer and the gel pad not only reduces the material costs, but also simplifies the method of production of the electrode.

A second or modified version of the electrode 170 is illustrated in FIGS. 26 and 27, said modified design being designated 170'. In this regard, the electrode 170' includes a semi-flexible plastic-like sheet 172' with terminal means formed thereon preferably in the form of a printed ink conductive pattern 174' having a terminal portion 176' and a conductor portion 178'. In place of the tab segment 180 which extends from the periphery of the main portion 173 of the semi-flexible plastic-like sheet 172 of the electrode 170, shown in FIG. 24, the embodiment of FIGS. 26 and 27 utilizes a tab 180' in the form of a cut-out depending from the main segment of said sheet. The tab segment extends upwardly from said main segment of the sheet 172' for attachment to a connector 182', as shown.

The electrode 170' also utilizes the conductive adhesive layer 171', as discussed previously. In order to prevent adherence of the tab 180' to the double-sided adhesive layer 171', the tab 180 is coated with a medical grade of silicone or the like, during manufacture. Accordingly, upon application of the conductive adhesive layer 171', said tab 180' remains free of adhesion thereto, and can be lifted up out of the plane of the main segment of a flexible sheet 172' for attachment to the conductor. Therefore, except for the manner of forming the tab 180', the electrode 170' is essentially identical to that as discussed with regard to FIGS. 24 and 25.

Turning now to FIGS. 28 and 29, there is illustrated a multi-terminal electrode constructed in accordance with the concept of the invention as illustrated in FIGS. 24–27, said electrode being designated generally 192. The electrode 192 is of the type having a lead wire assembly 193 pre-attached thereto. Further, the electrode 192 includes a single sheet of semi-flexible plastic-like sheet material 194 having separate individual conductive patterns, 195 printed thereon. Each pattern 195 includes a terminal portion 196, and a conductor portion 198. The conductor portions 198 on each half of the semi-flexible plastic-like sheet extend in opposite directions toward each other, and terminate proximate a central segment of the sheet. At this location, a crimp-type terminal 197 connector carried on the end of each lead wire of the assembly 193 is engaged through the upper surface of the semi-flexible plastic-like sheet 194 and disposed in electrical contact with the conductor portion 198, of the conductive pattern 195 on the under surfaces of said semi-flexible plastic-like sheet 194. This connection being best shown in FIG. 29, which is a sectional view showing the electrode 192 engaged to the skin 90 of a patient.

As was the case with the electrode 170 and 170'; the electrode 192 includes a layer of conductive adhesive 199; FIG. 29 on the under surface of sheet 194. In practice, it is undesirable to have a junction of dissimilar metals such as the copper which may be used for the terminal connection 197 and the silver or silver chloride coating on the conductor portion 198 in association with the conductive adhesive 199, as there exists the danger of electrolytic corrosion. Therefore, the joint or connection of the terminal 197 with the conductor portion 198 is hermetically sealed by placement of a quantity of epoxy or wax, or some other substance, designated generally 200, over the point of connection on the under side of the sheet 194. The conductive adhesive layer 199 is then applied in overlying relation to the undersurface of the electrode, preferably over the entire electrode. If desired, said adhesive may be subject to zoned application, in whatever pattern desired, provided the terminal portions 196 of the conductive pattern 195 is covered.

While the drawings disclose and the preceding specification discusses various preferred embodiments of the invention, it is not the intent to limit said invention thereto. In this regard, it is contemplated that those skilled in the art and possessed of the present disclosure may develop various alternative forms of the invention, without departing from the spirit and scope of said invention, as defined in the appended claims.

The invention is claimed as follows:

1. A multi-terminal, disposable medical electrode construction of the type adapted to be adhered to the skin of a patient for operative connection to electrical apparatus such as an electrocardiograph, an electromyograph, nerve or muscle stimulator, or the like, said multi-terminal electrode construction comprising, a pair of separate support members, each having one or more apertures formed therein, and one surface thereof including at least a partial adhesive coating for adhering the electrode to the skin of a patient; a single, semi-flexible sheet of plastic-like material affixed to an opposite surface of each said separate support member; terminal means for transmitting electrical signals on said semi-flexible sheet material, said terminal means providing terminal portions corresponding in number to, and in positional alignment with the apertures formed in said separate support members, such that the respective support members of said multi-terminal electrode construction are effectively joined in assembled relation by said semi-flexible sheet, with said sheet providing a hinge between the respective separate support members, enabling the support members to flex independently with respect to each other to conform to the contour of the patient.

2. A multi-terminal electrode construction according to claim 1, further including a sheet of release liner material, having a release coating on each side thereof, said sheet of release liner material being disposed between said support members, with one said support member engaged with each side of said sheet to bring the adhesive coating on the respective support members into contact with the sheet of release liner material such that upon use, the respective support members may be disengaged from said release liner, said release liner discarded and the electrode construction applied to the skin of patient.

3. A multi-terminal disposable medical electrode according to claim 1 wherein each said support member is provided by a first sheet of relatively thick, closed cell foam material, and affixed to each said first sheet is a second sheet of relatively thin foam material having an adhesively coated surface, said second sheet overlying portions of said semi-flexible sheet and the associated first sheet to affix said semi-flexible sheet to said first sheet of relatively thick, closed cell foam material.

4. A multi-terminal disposable medical electrode according to claim 3, wherein said semi-flexible sheet includes a plurality of relatively narrow extensions with a terminal portion being formed on each extension, each said extension having a width less than the diameter of the associated aperture in the support member, such that interiorly of each said aperture there exists exposed portions of the adhesive coating on said second relatively thin foam sheet, and a porous matrix disposed in each aperture in engagement with said exposed portions of the adhesive coating to retain said matrix in position.

5. A multi-terminal disposable medical electrode according to claim 4, wherein each said extension includes an aperture in the area of the terminal portion thereon which provides an additional exposed adhesive portion to which said porous matrix is secured.

6. A multi-terminal disposable medical electrode construction according to claim 1, further including a porous matrix disposed in each of said aperture, and a quantity of electrolytic gel impregnating each said porous matrix in association with said terminal portions.

7. A multi-terminal electrode construction according to claim 1, 3 or 6 wherein said terminal means is in the form of a thin pattern printed on one surface of said semi-flexible sheet with a conductive ink, said pattern including a plurality of individual terminal portions corresponding in number to and aligned with the apertures formed in said support members.

8. A multi-terminal disposable medical electrode according to claim 1, further including lead wire means for transmitting electric signals comprised of a plurality of lead wires each having a connector on one end thereof, which connectors are affixed to said semi-flexible sheet in conductive relation with said terminal means.

9. A multi-terminal electrode according to claim 8, wherein said terminal portions of the terminal means are provided by a pattern printed on a first surface of said semi-flexible sheet with a conductive ink, which pattern also includes individual, separate conductor portions associated with each terminal portion, said lead wire connectors being engaged through the semi-flexible sheet from the second surface thereof and engaged with the conductor portions of the terminal means, and a pair of sheets of relatively thin foam having an adhesively coated surface, one said sheet of thin foam overlying portions of a respective of one of said support members including portions of said semi-flexible sheet to adhesively secure said semi-flexible sheet to said support members, and said sheets of thin foam also overlying the connectors of said lead wire means to secure said connectors in place.

* * * * *